US012109295B2

(12) United States Patent
Cao et al.

(10) Patent No.: US 12,109,295 B2
(45) Date of Patent: Oct. 8, 2024

(54) COSMETIC COMPOSITIONS COMPRISING LOW MOLECULAR WEIGHT SILK FIBROIN

(71) Applicant: Conopco, Inc., Englewood Cliffs, NJ (US)

(72) Inventors: Han Cao, Shanghai (CN); Hong Chen, Shanghai (CN); Xin Chen, Shanghai (CN); Amitava Pramanik, Bangalore (IN); Zhengzhong Shao, Shanghai (CN); Jinrong Yao, Shanghai (CN); Weizheng Zhou, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 672 days.

(21) Appl. No.: 17/287,058

(22) PCT Filed: Oct. 8, 2019

(86) PCT No.: PCT/EP2019/077177
§ 371 (c)(1),
(2) Date: Apr. 20, 2021

(87) PCT Pub. No.: WO2020/083636
PCT Pub. Date: Apr. 30, 2020

(65) Prior Publication Data
US 2021/0378935 A1    Dec. 9, 2021

(30) Foreign Application Priority Data
Oct. 23, 2018   (WO) ................ PCT/CN2018/111503
Nov. 26, 2018   (EP) ..................................... 18208334

(51) Int. Cl.
A61K 8/64     (2006.01)
A61Q 5/00     (2006.01)
A61Q 5/02     (2006.01)

(52) U.S. Cl.
CPC ................ *A61K 8/64* (2013.01); *A61Q 5/002* (2013.01); *A61Q 5/02* (2013.01); *A61K 2800/805* (2013.01)

(58) Field of Classification Search
CPC .... A61K 8/64; A61K 2800/805; A61Q 5/002; A61Q 5/02
See application file for complete search history.

(56) References Cited

U.S. PATENT DOCUMENTS

| 7,193,038 | B2 | 3/2007 | Tsubouchi et al. | |
| 8,048,989 | B2 | 11/2011 | Tsukada et al. | |
| 8,481,681 | B2 | 7/2013 | Sutherland et al. | |
| 2002/0064539 | A1* | 5/2002 | Philippe | A61Q 1/02 514/20.7 |
| 2004/0219630 | A1* | 11/2004 | Tsubouchi | C07K 14/43586 435/68.1 |
| 2005/0143296 | A1 | 6/2005 | Tsuouchi et al. | |
| 2007/0041925 | A1 | 2/2007 | Picano et al. | |
| 2007/0190099 | A1 | 8/2007 | Dibenedetto et al. | |
| 2008/0107614 | A1* | 5/2008 | Fahnestock | C07K 7/08 514/1.3 |
| 2014/0086874 | A1 | 3/2014 | Nazhat et al. | |

FOREIGN PATENT DOCUMENTS

| CN | 1678339 A | 10/2005 |
| CN | 1769424 | 5/2006 |
| CN | 101168763 | 4/2008 |
| CN | 103468241 | 12/2013 |
| CN | 103993060 | 8/2014 |
| CN | 106580842 A | 4/2017 |
| CN | 106619172 | 5/2017 |
| JP | 55124793 | 9/1980 |
| JP | S60112710 | 6/1985 |
| JP | 7067686 | 3/1995 |
| JP | 2006292595 | 10/2006 |

(Continued)

OTHER PUBLICATIONS

Yohtaro Katagata, et al., Fractionation and Characterization of the Amorphous-Region Peptides of Fibroin Prepared from the Posterior Silk Gland, 53 J Seric. Sci. Jpn. 226 (Year: 1984).*
F Lucas et al.; Some amino acid sequences in the amorphous fraction of the fibroin of Bombyx mori; Biochemical Journal; Apr. 1, 1962; pp. 164-171; XP055551575; vol. 83, No. 1.
Katagata; Fractionation and Characterization of the amorphous-region peptides of fibroin prepared from the posterior silk gland; J Seric Sci Jpn; Feb. 1, 1984; pp. 226-236; XP055551592; vol. 53(3).
Search Report and Written Opinion in EP18208334; dated Feb. 18, 2019.
Search Report and Written Opinion in PCT application number; dated Dec. 4, 2019.
IPRP2 in PCTEP2019077177; dated Oct. 19, 2020.
Katagata, et al.; Characterixation of the crystalline-region peptides prepared from the posterior silk gland fibroin; J. Seric. Sci. Jpn.; 1984; pp. 165-174; 53(2).

(Continued)

Primary Examiner — Sean M Basquill
(74) Attorney, Agent, or Firm — Foley & Lardner LLP

(57) ABSTRACT

The invention relates to a cosmetic composition comprising a low molecular weight silk fibroin and a cosmetically acceptable carrier; wherein said low molecular weight silk fibroin comprises at least 85 parts by weight peptides of molecular weight less than 2500 Da, where amino acid sequence of at least 50 wt % of said peptides is GAGY, GAGAGAGY, GAGVGAGY or AWSSESDF and where said silk fibroin is produced by a process comprising the steps of: (i) mixing an aqueous solution comprising 0.01 to 20 wt % of a high molecular weight silk fibroin of weight average molecular weight 6 to 100 KDa with ochymotrypsin at temperature of 25 to 45° C., under pH of 6 to 9 for 4 to 24 hours; where ratio of said high molecular weight silk fibroin to said ochymotrypsin in said solution is from 100:1 to 300:1 parts by weight: (ii) inactivating excess ochymotrypsin and separating the inactivated α-chymotrypsin from reaction mixture of step (i); and (ill) drying said reaction mixture to obtain said low molecular weight silk fibroin; wherein said composition comprises 0.1 to 10% by weight of the low molecular weight silk fibroin.

6 Claims, No Drawings

(56) References Cited

FOREIGN PATENT DOCUMENTS

| JP | 2007191448 | 8/2007 |
|---|---|---|
| JP | 2007246461 | 9/2007 |
| JP | 2009089638 | 4/2009 |
| RU | 2467015 | 11/2012 |
| WO | WO2006033473 | 9/2005 |
| WO | WO2006014033 | 2/2006 |
| WO | WO2015070108 | 5/2015 |

OTHER PUBLICATIONS

Madyarov, et al.; A comparison of silk fibroin hydrolysates by hydrochlonic acis and proteolytic enzymes. I; Int. J. Industr. Entom; 2001; pp. 7-13 (ABSTRACT only); 2.

Lucas, et al.; Some amino acid sequences in the amorphous fraction of the fibroin of Bombyx mori.; Biochem. J.; 1962; pp. 164-171; 83.

Geddes, et al.; Mass spectrometric determination of the amino acid sequences in peptides isolated from the protein silk fibroin of Bombyx mori; Biochem. J. ; 1969; pp. 695-702; 114.

Lucas, et al.; The amino acid sequence in a fraction of the fibroin of Bombyx mori.; Biochem. J.; 1957; pp. 468-479; 66.

Zahn, et al.; Fractionation of the chymotryptic precipitate of Bombyx mori silk fibroin; Biochem. J; 1967; 1019-1025; 104.

Hyun, et al.; Hair care effects of hair cosmetics including low molecular weight silk peptide component and micro structure analysis; KSBB Journal; 2008; pp. 439-444 (Abstract Only); 23.

Hao, et al.; Characterization and assembly investigation of a dodecapeptide hydrolyzed from the crystalline domain of Bombyx mori silk fibroin.; Polym. Chem; 2013; pp. 3005-3011; 4.

Zhang, et al.; Self-assembly of a peptide amphiphile based on hydrolysed Bombyx mori silk fibroin; Chem. Commun; 2011; 10296-10298; 47.

Xu, et al.; Properties of elastase from Bacillus sp. EL31410 hydrolyzing soluble silk fibroin; Food Ferment. Ind.; 2008; pp. 28-31 (abstract only).

Li, et al.; Different types of peptide detected by mass spectrometry among fresh silk and archaeological silk remains for distinguishing modern contamination. ; PLoS ONE 10(7) (2015) e0132827; 2015; 1-9.

Hao, "Preparation of silk peptides and research on their assembly behavior", China Doctoral Dissertation Full Text Database, Engineering Science and Technology Series I, B014-63, Mar. 15, 2015, 3 pages.

Li et al., "Development, application and prospects of silk fibroin peptides", Sericulture Newsletter, vol. 28, No. 4, Dec. 31, 2008, 2 pages.

Sun et al., "New Fiber Materials", Shanhai University Press, Aug. 31, 2007, p. 335.

\* cited by examiner

COSMETIC COMPOSITIONS COMPRISING LOW MOLECULAR WEIGHT SILK FIBROIN

CROSS REFERENCE TO RELATED APPLICATIONS

The present application is a U.S. National Phase Application under 35 U.S.C. § 371 of International Application No. PCT/EP2019/077177, filed on Oct. 8, 2019, which claims priority to PCT/CN2018/111503 filed Oct. 23, 2018, and European Patent Application No. 18208334.5 filed on Nov. 26, 2018, the contents of each of which are incorporated herein in their entireties.

FIELD OF THE INVENTION

The present invention relates to a cosmetic composition comprising the low molecular weight silk fibroin.

BACKGROUND OF THE INVENTION

Silk fibroins are a kind of fibrous proteins present in silk and it somewhat resembles keratin (which is the main component of hair) in terms of fibrous structure. Besides, silk fibroin has good affinity to keratin due to intermolecular interactions such as hydrogen bonding and hydrophobic interactions. Therefore, silk fibroin is believed to exhibit good affinity towards keratin and has high potential for hair repair and enhancement. Generally, there are two major types of secondary structures in silk fibroin; a random coil which is water-soluble and a β-Sheet which is water-insoluble. In silk cocoon fibres, the highly oriented β-Sheet structure along the fibre axis contributes the most to the unique properties of silk fibre, including its smoothness, luster and strong mechanical strength.

Low molecular weight silk fibroins (short peptides) have attracted more attention due to their various advantages such as simple structure, biocompatibility and biodegradability. To cleave various peptide segments from the silk a number of efforts on enzymatic degradation of silk fibroin have been reported. However current commercial low molecular weight silk fibroin are mostly degradation products of silk fibroin with randomly degrading silk fibroin molecular chain which tends to lose its unique structure. Therefore, many desirable qualities or properties are lost. Therefore, there is a need for more efficacious cosmetic compositions that comprise low molecular weight silk fibroins.

JP7067686 A (Shinano Kenshi Co Ltd, 1995) relates to a process for producing a silk fibroin peptide having low molecular weight and useful for foods and cosmetics. This process is carried out by decomposing the high-molecular weight silk fibroin with a neutral inorganic acid, hydrolyzing the decomposition product with a proteinase to obtain an aqueous solution of low-molecular weight silk fibroin peptide and desalting the solution by electrodialysis.

JP60112710 A (Kanebo Ltd, 1983) discloses a composition containing a specific fibroin peptide and a liquid polyhydric alcohol, preventing the damage to hair, protecting hair from the chemical and mechanical stimulation, and capable of imparting good feel, luster, combing property and setting effect of the hair. Such fibroin peptides have an average molecular weight of 300 to 3500 Da, and can be prepared by hydrolysis of silk fibroin with an enzyme, an acid or an alkali.

US2007041925 A (Beiersdorf AG, 2007) relates to cosmetic preparations, especially hair care preparations or hair care products containing protein hydrolysates of silk, pashmina, cashmere wool, merino wool and/or mohair, mussel thread extracts, bysuss threads, and sericin and/or sericin hydrolysates. One example of hydrolyzed silk protein disclosed is Silkpro®. Such silk fibroin can be obtained by acidic, alkaline or enzyme hydrolysis of *Bombyx mori* cocoons.

SUMMARY OF THE INVENTION

The present inventors have developed specific low molecular weight silk fibroin prepared by enzymolysis using a selected enzyme. The process allows to retain the unique sequences of certain peptides from the original higher molecular weight silk fibroin chains by cleaving only certain selective sites of the high molecular weight silk fibroin chain. It is surprisingly observed that the low molecular silk fibroin not only deposits well on the surface of hair fibres but also penetrates into the core of the fibres. Therefore, it is able to deliver several benefits such as hair repairing, protection and lubrication.

In accordance with a first aspect is a cosmetic composition comprising a low molecular weight silk fibroin and a cosmetically acceptable carrier; wherein said low molecular weight silk fibroin comprises at least 85 parts by weight peptides of molecular weight less than 2500 Da, where amino acid sequence of at least 50 wt % of said peptides is GAGY, GAGAGAGY, GAGVGAGY or AWSSESDF and where said silk fibroin is produced by a process comprising the steps of:
   (i) mixing an aqueous solution comprising 0.01 to 20 wt % of a high molecular weight silk fibroin of weight average molecular weight 6 to 100 KDa with α-chymotrypsin at temperature of 25 to 45° C., under pH of 6 to 9 for 4 to 24 hours, where ratio of said high molecular weight silk fibroin to said α-chymotrypsin in said solution is from 100:1 to 300:1 parts by weight;
   (ii) inactivating excess α-chymotrypsin and separating the inactivated α-chymotrypsin from reaction mixture of step (i); and
   (iii) drying said reaction mixture to obtain said low molecular weight silk fibroin;
Wherein said composition comprises 0.1 to 5% by weight of the low molecular weight silk fibroin.

In accordance with a second aspect is disclosed a method for modifying at least one surface characteristic of hair fibres comprising a step of topical application of said cosmetic composition of the first aspect.

In accordance with a third aspect is disclosed a method for modifying at least one internal feature of hair fibres comprising a step of topical application of said cosmetic composition of the first aspect.

Yet another aspect of the present invention provides for use of a hair care composition of the second aspect for modifying at least one internal feature of hair fibres.

All other aspects of the present invention will more readily become apparent upon considering the detailed description and examples which follow.

Except in the examples, or where otherwise explicitly indicated, all numbers in this description indicating amounts of material or conditions of reaction, physical properties of materials and/or use may optionally be understood as modified by the word "about".

All amounts are by weight of the cosmetic composition, unless otherwise specified.

It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

DETAILED DESCRIPTION OF THE INVENTION

By "a cosmetic composition" as used herein, is meant to include a composition for topical application to the skin of mammals, especially human beings. Such a composition may be generally classified as leave-on or rinse off but is preferably of the leave on type. The composition is formulated into a product which is applied to a human body specifically for improving appearance but may, in addition, also provide cleansing, odor control or general aesthetics. The composition of the present invention can be in the form of a liquid, lotion, cream, foam, scrub, gel, or toner, or applied with an implement or via a face mask or a pad. Non-limiting examples of such compositions include leave-on skin lotions, creams, antiperspirants, deodorants, lipsticks, foundations, mascara, sunless tanners and sunscreen lotions. The composition of the present invention is preferably a leave-on composition. "Skin" as used herein is meant to include skin on the face and body (e.g., neck, chest, back, arms, underarms, hands, legs, buttocks and scalp) and especially to the sun exposed parts thereof.

By 'A Hair Care Composition" as used herein, is meant to include a composition for topical application to hair and/or scalp of mammals, especially humans. Such a composition may be generally classified as leave-on or rinse off, and includes any product applied to a human body for also improving appearance, cleansing, odour control or general aesthetics. The composition of the present invention can be in the form of a liquid, lotion, cream, foam, scrub, gel, or bar. Non-limiting examples of such compositions include leave-on hair lotions, creams, and wash-off shampoos, conditioners, shower gels, or toilet bar. When the cosmetic composition of the present invention is a hair care composition, it preferably is a wash-off composition, especially preferred being a shampoo or a conditioner.

Low Molecular Weight Silk Fibroin

Low molecular weight silk fibroin comprising at least 85 parts by weight peptides of molecular weight less than 2500 Da, where amino acid sequence of at least 50 wt % of said peptides is GAGY, GAGAGAGY, GAGVGAGY or AWSSESDF is produced by a process comprising the steps of:
(i) mixing an aqueous solution comprising 0.01 to 20 wt % of a high molecular weight silk fibroin of weight average molecular weight 6 to 100 KDa with α-chymotrypsin at temperature of 25 to 45° C., under pH of 6 to 9 for 4 to 24 hours, where ratio of said high molecular weight silk fibroin to said α-chymotrypsin in said solution is from 100:1 to 300:1 parts by weight;
(ii) inactivating excess α-chymotrypsin and separating the inactivated α-chymotrypsin from reaction mixture of step (i); and
(iii) drying said reaction mixture to obtain said low molecular weight silk fibroin.

Preferably, the aqueous solution of step (i) comprises 0.1 to 10 wt % of the high molecular weight silk fibroin along with α-chymotrypsin. Preferably, the ratio of the high molecular weight silk fibroin to said α-chymotrypsin in step (i) is from 150:1 to 250:1 parts by weight.

It is preferred that the temperature in step (i) is from 30 to 45° C. Preferably, the pH of the aqueous solution of step (i) is from 8 to 9. Further, preferably the heating process lasts for 6 to 15 hours.

The low molecular weight silk fibroin in accordance with this invention comprises at least 85 parts by weight peptides of molecular weight less than 2500 Da, preferably at least 95 parts by weight peptides of molecular weight less than 2500 Da, more preferably at least 95 parts by weight peptides of molecular weight less than 2000 Da. It is preferred that the low molecular weight silk fibroin in accordance with this invention comprises at least 85 parts by weight peptides of molecular weight from 150 to 2500 Da, more preferably at least 85 parts by weight peptides of molecular weight from 150 to 2000 Da. The amino acid sequence of at least 50 wt % of the peptides is GAGY, GAGAGAGY, GAGVGAGY or AWSSESDF.

For the sake of clarity, it is hereby clarified that the meaning of the terms is as follows:
A: Alanine
D: Aspartic acid
E: Glutamic acid
F: Phenylalanine
G: Glycine
S: Serine
W: Tryptophan
Y: Tyrosine It is well-known that tyrosine in keratin associated proteins interacts with arginine in intermediate filament protein by cation-π interactions and boosts the dimerization and helical arrangement of intermediate filament proteins, thus improving the properties of hair fibres. Therefore, it is preferred that the low molecular weight silk fibroin of the invention comprises tyrosine and the mole fraction of tyrosine in the low molecular weight silk fibroin is not less than 10 mol %. More preferably this mole fraction is from 10 mol % to 32 mol %.

In order to be formulated easily into cosmetic compositions, it is preferred that solubility of the low molecular weight silk fibroin in accordance with this invention is from 11 to 42 g/100 g water.

Without wishing to be bound by theory, the inventors believe that α-chymotrypsin cleaves only certain sites of the original high molecular weight silk fibroin molecular chains under the specific conditions of the process. Therefore, the unique sequences in the high molecular weight silk fibroin can be kept intact, thereby resulting in low molecular weight silk fibroins having the potential to form β-sheet structure, so as to provide better hair care benefits such as hair repairing, lubrication and protection.

Cosmetic Compositions

In accordance with a first aspect is disclosed a cosmetic composition comprising the low molecular weight silk fibroin of the invention and a cosmetically acceptable carrier. It is preferred that the cosmetic composition is a hair care composition. It is more preferred that when the cosmetic composition of the invention is a hair care composition, it is a shampoo, a hair conditioner or a leave on hair care composition. It is most preferred that the hair care composition is a shampoo.

It is preferred that the composition comprises from 0.1 to 10 wt %, more preferably, from 0.1 to 5 wt %, most preferably from 0.1 to 2 wt % by weight of said low molecular weight silk fibroin, based on total weight of the composition.

The cosmetic composition of the invention comprises a cosmetically acceptable carrier. The ingredients of the carrier depend on the nature of the composition. The most preferred carrier is an emulsion. Emulsions are mixtures, usually thermodynamically stable mixtures of oil and water. The emulsion may be an oil-in-water emulsion or a water-in-oil emulsion or a more complex emulsion. Emulsions are generally stabilized using emulsifiers of which organic surfactants are the most common type. The emulsion as per the present invention is preferably an oil-in-water emulsion. The oil used to prepare the emulsion is preferably selected from vegetable oil, mineral oil, silicone oil or mixtures thereof. The vegetable oil is preferably selected from one or more of palm oil, canola oil, corn oil, neem oil, olive oil, cottonseed oil, coconut oil, fractionated coconut oil, nut oils, safflower oil, sesame oil, soybean oil or sunflower oil. Oil is preferably included in 0.1 to 20 wt % preferably 0.5 to 15 wt % by weight of the composition.

The cosmetic composition of the invention, especially when in the form of a hair care composition such as a shampoo preferably comprises an anionic surfactant e.g. an alkyl sulphate and/or ethoxylated alkyl sulfate surfactant. These anionic surfactants are preferably present at a level of from 2 to 16 wt %, more preferably from 3 to 16 wt % by weight of the composition. Preferred alkyl sulfates are C8 to 18 alkyl sulfates, more preferably C12 to 18 alkyl sulfates, preferably in the form of a salt with a solubilizing cation such as sodium, potassium, ammonium or substituted ammonium. Examples are sodium lauryl sulfate (SLS) and sodium dodecyl sulfate (SDS).

Preferred alkyl ether sulfates are those having the formula: RO(CH2CH2O) nSO$_3$M; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilizing cation such as sodium, potassium, ammonium or substituted ammonium. An example is sodium lauryl ether sulfate (SLES).

Preferred ethoxylated alkyl sulfate anionic surfactant is sodium lauryl ether sulfate (SLES) having an average degree of ethoxylation of from 0.5 to 3, preferably 1 to 3.

The cosmetic composition as per the invention optionally and preferably additionally comprises a betaine surfactant. In a preferred embodiment, the composition comprises from 0.1 to 10 wt %, preferably from 0.5 to 8 wt %, more preferably from 1 to 5 wt % of a betaine surfactant, preferably an alkyl amidopropyl betaine, for example cocamidopropyl betaine.

Shampoo compositions according to the invention may comprise one or more further anionic cleansing surfactants which are cosmetically acceptable and suitable for topical application to the hair.

Examples of further suitable anionic cleansing surfactants are the alkaryl sulphonates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule. Typical anionic cleansing surfactants for use in shampoo compositions of the invention include sodium oleyl succinate, ammonium lauryl sulphosuccinate, sodium lauryl ether sulphosuccinate, sodium dodecylbenzene sulphonate, triethanolamine dodecylbenzene sulphonate, lauryl ether carboxylic acid and sodium N-lauryl sarcosinate.

Suitable preferred additional anionic cleansing surfactants are sodium lauryl ether sulphosuccinate(n)EO, (where n is from 1 to 3), lauryl ether carboxylic acid (n) EO (where n is from 10 to 20).

Mixtures of any of the foregoing anionic cleansing surfactants may also be suitable.

If added, the total amount of anionic cleansing surfactant in shampoo compositions of the invention may generally range from 0.5 to 45 wt %, preferably from 1.5 to 35 wt %, more preferably from 5 to 20 wt %, calculated by total weight % of the anionic cleansing surfactant based on the total weight of the composition.

When the cosmetic composition of the invention is a hair conditioning composition, it preferably comprises conditioning surfactants selected from cationic surfactants, used singly or in admixture. Preferably, the cationic surfactants have the formula N$^+$R1R2R3R4 wherein R1, R2, R3 and R4 are independently (C1 to C30) alkyl or benzyl. Preferably, one, two or three of R1, R2, R3 and R4 are independently (C4 to C30) alkyl and the other R1, R2, R3 and R4 group or groups are (C1-C6) alkyl or benzyl. More preferably, one or two of R1, R2, R3 and R4 are independently (C6 to C30) alkyl and the other R1, R2, R3 and R4 groups are (C1-C6) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g., oleyl). Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant. Yet another preferred cationic surfactant is stearamidopropyl dimethylamine.

The most preferred cationic surfactants for use in the composition are stearamidopropyl dimethylamine, behentrimonium chloride, or stearyl trimethyl ammonium chloride. In conditioners of the invention, the level of cationic surfactant will generally range from 0.1 to 5 wt %, preferably 0.5 to 2.5 wt % by weight of the composition.

Hair conditioning compositions of the invention preferably may also additionally comprise a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.5 to 10 wt %, preferably from 0.1 to 8 wt %, more preferably from 0.2 to 7 wt %, most preferably from 0.3 to 6 wt % by weight of the composition. The weight ratio of cationic surfactant to fatty alcohol is preferably from 1:1 to 1:10, more preferably from 1:1.5 to 1:8, and optimally from 1:2 to 1:5.

According to another aspect of the present invention, the cosmetic composition of the may be delivered as a leave on composition. In such cases, the additional surfactants and other actives used to deliver the product as a shampoo or a conditioner may not be required. The cosmetically acceptable vehicle in such a product may simply be water or water structured with polymers.

Method and Use

The present invention provides for a method of modifying at least one surface characteristic of hair fibres comprising a step of topical application of the cosmetic composition of the first aspect of the invention.

The present invention provides for a method of modifying at least one internal feature of hair fibres comprising a step of topical application of the cosmetic composition as claimed in the first aspect of the invention.

The invention also provides for use of the hair care composition of the first aspect of the invention for modifying at least one surface characteristic of hair fibres. Preferably, the surface characteristic is lubricity of hair-fibres.

The invention also provides for use of the hair care composition of the first aspect of the invention for modifying at least one internal feature of hair fibres. Particularly, the internal feature means at least one of deep hair repairing or hair strengthening The use in accordance with the invention is preferably non-therapeutic in nature, more preferably cosmetic in nature.

The invention will now be illustrated with the help of the following non-limiting examples.

EXAMPLES

Example 1

A variety of low molecular weight silk fibroins as detailed in Table-1 were prepared by a process that is described hereinafter. Low molecular weight silk fibroin of Reference No. 1 is in accordance with the present invention. Rest of the silk fibroins were not.

After preparing put through some tests as detailed hereinafter:

TABLE 1

| Reference No. | Average Molecular weight (kDa) | Enzyme/agent used for preparation of low molecular weight silk fibroin | Supplier of the low molecular weight silk fibroin (where applicable) |
| --- | --- | --- | --- |
| 1 | Less than 2 kDa | α-chymotrypsin | Prepared in house |
| A | Less than 2 kDa | Elastase | Prepared In house |
| B | Less than 2 kDa | Alkaline protease | Prepared In house |
| C | Less than 2 kDa | Acid (not an enzyme) | Commercially procured from Xintiansi Co |
| D | Less than 0.5 kDa | Alkaline protease | Commercially procured from Xintiansi Co |

Low molecular weight silk fibroins (Reference No. 1, A and B) from in house were prepared by the following process with the corresponding enzyme as indicated in Table 1:

(i) A 4% aqueous solution of high molecular weight (95 kDa) silk fibroin was prepared by using following process:

Degumming: raw *Bombyx mori* silkworm cocoons were boiled in 0.5 wt % sodium carbonate solution twice (each 20 minute) to remove sericin.

Dissolving: the degummed dry silk was dissolved in 9.5 mol/L lithium bromide aqueous solution at 40° C. for 40 minutes.

Purifying: after being filtered, the solution was dialyzed against deionized water for 72 hours at room temperature with a 12-14 kDa molecular weight cut-off dialysis membrane to remove the salt. The dialyzed solution was then clarified by centrifuging at 8,000 rpm for 8 minutes. The supernatant which was an aqueous silk fibroin solution was collected and stored at 4° C. before use.

(ii) The concerned enzyme was then added to the solution of high molecular weight silk fibroin. The ratio of the high molecular weight silk fibroin to the enzyme was maintained at 200:1 parts by weight for each experiment. The pH was adjusted to 8.5, and the reaction was allowed continued for 8 hours at 37° C.

(iii) The reaction mixture of step (ii) was heated to 85° C. and kept aside for 15 minutes to inactivate the enzyme and the inactivated enzyme was then separated from the reaction mixture.

(iv) The reaction mixture was then dried to obtain the corresponding low molecular weight silk fibroin.

Characterization of Low Molecular Weight Silk Fibroin

Gel permeation chromatography (GPC) is an analytical technique that separates molecules and provides the molecular weight distribution of a material. The molecular weight distribution of low molecular weight silk fibroins (Reference No. 1 and A) were measured by it and shown in Table-2 below.

TABLE 2

| | Molecular weight distribution (area %); Note: k indicates thousand MW (Da) | | | | | |
|---|---|---|---|---|---|---|
| Reference No. | above 3k | 3k to 2k | 2k to 1k | 1k to 500 | 500 to 180 | less than 180 |
| 1 | 1.03% | 1.36% | 4.05% | 13.40% | 69.73% | 10.44% |
| A | 0.26% | 0.51% | 1.80% | 5.99% | 73.43% | 18.01% |

The data in Table-2 above indicates that at least 85% of low molecular weight silk fibroins (Reference No. 1 and A) had molecular weight less than 2500 Da.

Main peptides of the low molecular weight silk fibroins (Reference No. 1 and A) were evaluated by HPLC-MS and shown in Table-3 below:

TABLE 3

| Reference No. of the low molecular silk fibroin | Main peptides | Molecular weight |
|---|---|---|
| 1 | GAGY | 366 |
| | GAGAGAGY | 622 |
| | GAGVGAGY | 650 |
| | AWSSESDF | 927 |
| A | $G_3A_2S_1$ (GAGAGS or GAGSGA or GSGAGA, or other combinations) | 418 |
| | $G_3A_3$ (GAGAGA or other combinations.) | 402 |
| | $G_4A_3S_1$ (GAGAGAGS or GAGAGSGA or other combinations) | 546 |
| | $G_6A_4S_2$ (GAGSGAGAGSGA or other combinations) | 818 |

The data in Table-3 above indicates that low molecular weight silk fibroin as per the invention (Reference No. 1) comprises peptides with low molecular weight, and the amino acid sequence of at least 50 wt % of the main peptides is GAGY, GAGAGAGY, GAGVGAGY or AWSSESDF.

The weight percentage of the amino acid sequence of these peptides was calculated by using a theoretical method as follows:

The high molecular weight silk fibroin has an amphiphilic structure consisting of hydrophobic repetitive domains and hydrophilic non-repetitive domains. After hydrolysis by α-chymotrypsin, the sequences of hydrophobic repetitive domains will assemble to insoluble aggregates (which is removed by centrifugation, with about 60% of weight). The most components in supernatant are from hydrophilic non-repetitive domains (non-crystal region of heavy chain, with 40% of weight).

The theoretical molecular weight of the high molecular weight silk fibroin (with 5263 of amino acid residues) of silk fibroin is 391593. GAGAGAGY (molecular weight: 622), a typical sequence in the α-chymotrypsin hydrolysed fibroin product (supernatant part), can be found 54 times in the chain of high molecular weight silk fibroin. Then the calculated weight fraction of GAGAGAGY=54*622/(391593*40%)=21.4%. The weight percentage of other peptides was calculated by using the same method. The result is summarized in the Table-4 below:

TABLE 4

| Amino acid sequence of Reference No. 1 | Molecular weight/ Daltons | Repeated number | wt% |
|---|---|---|---|
| GAGY | 366 | 99 | 23.1% |
| GAGAGAGY | 622 | 54 | 21.4% |
| GAGVGAGY | 650 | 31 | 12.9% |
| AWSSESDF | 927 | 8 | 4.7% |
| Total | | | 62.1% |

Tyrosine content of each silk fibroin of Table 1 was evaluated by L-8900 Amino Acid Analyzer (Hitachi Co.). The mol percentage of tyrosine (including free tyrosine and tyrosine contained in peptides) in the low molecular weight silk fibroins is calculated and summarized in Table-5 below:

TABLE 5

| Reference No. of silk fibroin | Tyrosine content |
|---|---|
| 1 | 10.29 mol % |
| A | 5.52 mol % |
| B | 5.42 mol % |
| C | 0.07 mol % |
| D | 0.09 mol % |

The data in Table-5 above indicates that low molecular weight silk fibroin as per the invention (Reference No. 1) comprises higher mole fraction of tyrosine; greater than 10 mol %.

Example 2

Hair Care Benefits of Low Molecular Weight Silk Fibroin

Hair switches: Chinese black hair switches were commercially received from IHIP Co. Treatment of hair switches with low molecular weight silk fibroin:

Pre-Treatment:

The hair switches were washed with 14% SLES base by applying the base solution (0.1 mL/g hair) evenly down the length of the switch, then holding both ends of the switch and gently massaging the base solution into the hair for 30 seconds. Afterwards, rinsing for 30 seconds by running the fingers down the switch every 5 seconds and by removing excess water. Then the process was repeated and the hair switches were dried overnight at 20° C./50% relative humidity.

Soak Treatment:

The pre-treated hair switches were immersed in solution of the concerned low molecular weight silk firoin (1%) for 1 hour.

Deposition and Penetration of the Low Molecular Weight Silk Fibroin as Per the Invention on Hair Fibre:

To validate the deposition of low molecular weight silk fibroin as per the invention (Reference No. 1) onto the surface of hair fibres and investigate whether it could penetrate into the core of the hair fibre, the hair fibres were treated (soak treatment) with rhodamine B labelled low molecular weight silk fibroin as per the invention (Reference No. 1). The surfaces and cross-sections of hair fibres before and after the treatment were observed by fluorescence microscope (IX71, Olympus, Japan) and laser scanning confocal microscope (C2+, Nikon, Japan) respectively. To obtain cross-section images of the hair fibres, they were embedded in an epoxy resin and cut into slices by a microtome (FC7-UC7, Leica, Germany).

It was observed that both virgin and bleached hair were nearly invisible in fluorescent image, while the outer layer and inner part of bleached hair treated with low molecular weight silk fibroin as per the invention (Reference No. 1) exhibited strong red fluorescence, confirming deposition of low molecular weight silk fibroin on the surface of hair fibres and penetration into the core. This was an important observation because penetration of actives is necessary for any repair of hair fibres.

Effect of the Low Molecular Weight Silk Fibroin on Hair Damage Repairing:

As reported in literature, bleached hair fibres usually have lower denaturation temperature compared with virgin hair fibres, and the denaturation temperature increases (or returns to normal) when the damage is repaired. Differential Scanning Calorimetry (DSC) is a sensitive method commonly used to assess hair damage and the corresponding damage repairing effects. DSC was employed to characterize the denaturation temperature of damaged and treated hair fibres.

Bleached hair switches were immersed in solutions (1%) with low molecular weight silk fibroin from Table-1 respectively for 1 hour.

Hair switches were evenly divided into five segments from root to tip; each segment was 4 cm. Hair in each segment was finely cut into very small pieces and mixed sufficiently. 5 to 7 mg of small hair pieces were put into middle pressure crucible, then 50 μL of Milli-Q® Water was added and after 12 hours they were tested by DSC (Mettler, Switzerland). The program was: 50 to 100° C., 10° C./min, hold for 3.0 minutes, 100 to 180° C., 5° C./minutes.

The data is summarized in Table-6 below.

TABLE 6

| | Hair switches | | | | | | |
|---|---|---|---|---|---|---|---|
| | Bleached hair treated with low molecular weight silk fibroin | | | | | Bleached hair without treatment | Virgin hair |
| | Reference No. of silk fibroin | | | | | | |
| | 1 | A | B | C | D | NA | NA |
| Denaturation temperature (° C.) | 148.7 | 146.5 | 146.1 | 147.1 | 146.7 | 144.7 | 150.2 |

The data in Table-6 indicates that the denaturation temperature increases the most after the bleached hair fibres were treated with the low molecular silk fibroin as per the invention (Reference No. 1). It indicates that the low molecular silk fibroin as per the invention provides for better damage repair for the inherent strength of the hair as compared to the low molecular silk fibroins outside the invention (Reference No. A to D).

Example 3

Hair Care Benefit of the Hair Care Composition as Per the Invention

The following hair care compositions as shown in Table-7 were prepared. Reference number of the composition in accordance with the invention was Reference No. 2.

TABLE 7

| | Reference No. of the composition | |
|---|---|---|
| Ingredients/wt % | 2 | E |
| Low molecular weight silk fibroin (Reference No. 1) | 2.0 | 0 |
| Sodium laureth sulfate (SLES) | 17.1 | 17.1 |
| Coco amidopropyl betaine (CAPB) | 5.3 | 5.3 |
| Water and other minors | To 100 | To 100 |

Effect of the Hair Care Composition as Per the Invention on Hair Damage Repairing:

Hair switches were treated with one wash with the hair care compositions following the procedure as detailed hereinafter.

The composition (0.1 mL/g hair) was applied evenly down the length of the switch, then holding both ends of the switch and gently massaging the composition into the hair for 30 seconds. Afterwards, the hair switches were rinsed for 30 seconds by running the fingers down the switch every 5 seconds and removing excess water. Then the hair switches were dried overnight at 20° C./50% relative humidity.

The denaturation temperature of the hair switches was measured using DSC following the procedure described earlier. The data is summarized in Table-8.

TABLE 8

| Hair switches | Bleached hair treated with composition | | Bleached hair without treatment | Virgin hair |
|---|---|---|---|---|
| Reference No. of composition | 2 | E | NA | NA |
| Denaturation temperature (° C.) | 148.91 | 148.36 | 147.95 | 151.13 |

The data in Table-8 above shows that the bleached hair fibres have higher denaturation temperature after being treated with the composition as per the invention (Reference No. 2) which comprises the low molecular weight silk fibroin as compared to the ones treated with the composition without low molecular weight silk fibroin (Reference No. E). It indicates that the hair care composition as per the invention (Reference No. 2) provides for better damage repair for the inherent strength of the hair.

Effect of the Hair Care Composition as Per the Invention on Hair Protection:

Hair switches were treated with one wash with the hair care compositions following the procedure described above.

The hair switches were combed automatically by Hair Life Cycle Rig (HLCR) for 5000 strokes, and the number of broken fibres were counted. Five replicate hair switches were tested for each treatment. The data is summarized in Table-9 below.

TABLE 9

| Hair switches | Bleached hair treated with composition | Bleached hair without treatment | Virgin hair |
|---|---|---|---|
| Reference No. of composition | 2 | E | NA | NA |
| Number of broken hair fibres | 12 ± 4 | 82 ± 19 | 240 ± 35 | 127 ± 24 |

The data in Table-9 above shows that the number of broken hair fibres decreased dramatically after being treated with the composition as per the invention (Reference No. 2) which comprises the low molecular weight silk fibroin It indicates that the hair care composition as per the invention (Reference No. 2) provides for better hair protection benefits.

The invention claimed is:

1. A cosmetic composition comprising a low molecular weight silk fibroin and a cosmetically acceptable carrier; wherein:
   said low molecular weight silk fibroin comprises:
      peptides of molecular weight less than 2500 Da, where the amino acid sequence of at least 50 wt % of said peptides is GAGY, GAGAGAGY, GAGVGAGY or AWS SESDF;
      tyrosine and its mole fraction in said low molecular weight silk fibroin is not less than 10 mol %; and
   is produced by a process comprising the steps of:
      (i) mixing an aqueous solution comprising 0.01 to 20 wt % of a high molecular weight silk fibroin of weight average molecular weight 6 to 100 KDa with α-chymotrypsin at temperature of 25 to 45° C., under pH of 6 to 9 for 4 to 24 hours, where ratio of said high molecular weight silk fibroin to said α-chymotrypsin in said solution is from 100:1 to 300:1 parts by weight;
      (ii) inactivating excess α-chymotrypsin and separating the inactivated α-chymotrypsin from reaction mixture of step (i); and,
      (iii) drying said reaction mixture to obtain said low molecular weight silk fibroin;
   said composition comprises 0.1 to 10 wt % by weight of the low molecular weight silk fibroin and includes any product applicable to the human body for improving appearance, cleansing, odor control, or general aesthetics.

2. The cosmetic composition as claimed in claim 1 wherein solubility of said low molecular weight silk fibroin in water is from 11 to 42 g/100 g water.

3. The cosmetic composition as claimed in claim 1 wherein said hair care composition is a shampoo.

4. The cosmetic composition as claimed in claim 1 wherein the composition comprises 0.1 to 5% by weight of said low molecular weight silk fibroin.

5. A method of modifying at least one internal feature of hair fibres comprising of topically applying the cosmetic composition of claim 1 to hair.

6. A method of modifying at least one surface characteristic of hair fibres comprising of topically applying the cosmetic composition of claim 1 to hair.

* * * * *